United States Patent [19]

Marshall et al.

[11] Patent Number: 5,191,142
[45] Date of Patent: Mar. 2, 1993

[54] PROCESS FOR CONVERTING METHANOL TO OLEFINS OR GASOLINE

[75] Inventors: Christopher L. Marshall; Jeffery T. Miller, both of Naperville, Ill.

[73] Assignee: Amoco Corporation, Chicago, Ill.

[21] Appl. No.: 812,640

[22] Filed: Dec. 23, 1991

[51] Int. Cl.$^5$ ............................................. C07C 1/00
[52] U.S. Cl. .................................. 585/640; 585/638; 585/639
[58] Field of Search .................... 585/638, 639, 640

[56] References Cited

U.S. PATENT DOCUMENTS

| | | | |
|---|---|---|---|
| 3,894,107 | 7/1975 | Butter et al. | 585/640 |
| 3,931,349 | 1/1976 | Kuo | 260/668 R |
| 3,998,899 | 12/1976 | Daviduk et al. | 260/668 R |
| 4,035,430 | 7/1977 | Dwyer et al. | 260/668 R |
| 4,268,420 | 5/1981 | Klotz | 252/432 |
| 4,269,813 | 5/1981 | Klotz | 423/277 |
| 4,285,919 | 8/1981 | Klotz et al. | 423/277 |
| 4,447,669 | 5/1984 | Hamon et al. | 585/640 |
| 4,467,133 | 8/1984 | Chang et al. | 585/640 |
| 4,496,785 | 1/1985 | Miller et al. | 585/640 |
| 4,645,864 | 2/1987 | Chang et al. | 585/408 |
| 4,709,113 | 11/1987 | Harandi et al. | 585/640 |
| 4,788,365 | 11/1988 | Harandi et al. | 585/312 |
| 4,788,369 | 11/1988 | Marsh et al. | 585/409 |
| 5,028,400 | 7/1991 | Harandi et al. | 585/640 |

FOREIGN PATENT DOCUMENTS 068796 9/1986 European Pat. Off. .

OTHER PUBLICATIONS

Chang, "Hydrocarbons for Methanol", Catal. Rev.-Sci. Eng., vol. 25, No. 1, pp. 1-118 (1983).

Primary Examiner—Patrick P. Garvin
Assistant Examiner—E. D. Irzinski
Attorney, Agent, or Firm—Scott P. McDonald; Richard A. Kretchmer; Frank J. Sroka

[57] ABSTRACT

A process for efficiently converting methanol to $C_3$-$C_{12}$ olefins or paraffinic gasoline components is disclosed. A gaseous reaction mixture containing methanol and olefins is contacted with a solid acid catalyst in a reaction zone under conditions whereby a positive methanol concentration is maintained throughout the reaction zone. The process provides extended catalyst life, reduced deactivation rates, improved yields, and enhanced selectively for valuable products.

29 Claims, No Drawings

5,191,142

PROCESS FOR CONVERTING METHANOL TO OLEFINS OR GASOLINE

BACKGROUND OF THE INVENTION

1. Field of the Invention

This invention relates to a process for converting methanol to olefins or gasoline and, more particularly, the invention is directed to a catalytic process for selectively converting methanol to olefins having at least three carbon atoms per molecule or paraffinic gasoline components.

2. Description of Related Technology

Diminishing supplies of high quality crude oil feedstocks have resulted in investigations of alternative sources of hydrocarbons to be used for conversion to gasoline or as constituents of gasoline. One such alternative has been the use of methanol as a primary fuel additive for gasoline, and as a feedstock for the production of gasoline.

In the past, a typical route for conversion of methanol to gasoline has been through the use of so-called "shape selective" catalysts such as ZSM-5 aluminosilicates and AMS-1B and HAMS-1B borosilicates, which have been shown to have a strong selectivity for high octane gasoline components and additionally are characterized as having a slow deactivation rate via coke formation. The slow rate of coke formation is believed to result from the relatively small diameter of such catalysts' pores, which do not allow sufficient hydrocarbon polymerization to result in a high coking rate.

In the past, catalytic cracking catalysts containing faujasite Y-zeolites have also been investigated as methanol conversion catalysts. As used in the past, such catalysts have lower activity and a faster deactivation rate via coke formation than corresponding shape selective catalysts. Additionally, faujasite Y-zeolites generally gave higher yields of light $C_1-C_4$ hydrocarbons. As a result, faujasite Y-zeolites have often been overlooked as methanol conversion catalysts.

SUMMARY OF THE INVENTION

It is an object of the invention to overcome one or more of the problems described above.

According to the invention, a process for converting methanol to valuable olefins or paraffinic gasoline components is provided wherein a solid acid methanol conversion catalyst and a gaseous reaction mixture comprising methanol and conversion products thereof are contacted in a reaction zone while maintaining a positive methanol concentration throughout the reaction zone. Preferably, a substantially homogeneous reaction mixture is maintained throughout the reaction zone.

The presence of methanol throughout the reaction mixture greatly enhances catalyst life and activity, and increases the catalyst selectivity for valuable olefins or gasoline fraction components, resulting in improved yield of products and higher conversion of methanol feed. The enhancement in activity allows the use of such catalysts as Y-zeolites and amorphous silica-alumina catalysts, for example, which in the past were considered to have insufficient activity and unacceptably high deactivation rates for methanol to gasoline or methanol to olefin conversion processes.

Other objects and advantages of the invention will be apparent to those skilled in the art from a review of the following detailed description, taken in conjunction with the appended claims.

DETAILED DESCRIPTION OF THE INVENTION

According to the invention, a methanol feedstream comprising at least one mole of methanol per mole of any olefins present in the feedstream is catalytically converted to a hydrocarbon product comprising valuable $C_3-C_{12}$ olefins (especially short chain non-aromatic olefins which provide high yields of liquid product) or paraffinic gasoline components (i.e. $C_4+$ hydrocarbons, especially $C_4-C_{12}$ paraffins, and particularly isoparaffins, depending on the choice of catalyst and reaction conditions) by contacting a reaction mixture comprising the feedstream and conversion products thereof with a solid acid methanol conversion catalyst in a reaction zone under methanol conversion conditions while maintaining a positive methanol concentration (and preferably a uniform reaction mixture composition) throughout the reaction zone.

The reaction may be conveniently carried out on a continuous basis, with or without recycle, in any convenient form of reactor such as in a backmixed fluidized bed, in a backmixed fixed bed reactor such as a continuous stirred tank (CSTR) fixed bed reactor, such as a Berty reactor, or in a plug flow reactor with recycle of product effluent through the reaction zone.

Backmixed fluidized bed reaction systems are preferred for ease of regenerability of catalysts in such systems.

The reaction is conveniently carried out at a temperature of about 600° to about 900° F., preferably about 675° to about 775° F., and highly preferably less than 750° F., and at atmospheric pressure in either a backmixed fixed or fluid bed reactor or at an elevated pressure of up to about 500 psig, and typically up to about 100 psig, particularly in a fixed bed CSTR reactor.

Relatively low weight hourly space velocities of about 0.1 to about 20 g/g cat./hour ($hr^{-1}$) are preferred with a weight hourly space velocity in the range of about 1 to about 5 $hr^{-1}$ being highly preferred.

Paraffinic gasoline production is favored over olefin production by the use of relatively high activity catalysts to obtain high conversion, relatively low space velocity (i.e. WHSV of about 0.1 to about 1.0 $hr^{-1}$, preferably less than about 0.5 $hr^1$), relatively high temperature (i.e. above about 800° F.), and/or relatively high proportions (i.e. greater than about 50 wt. %) of zeolite in the catalyst.

At temperatures less than about 600° F., methanol conversion activity is extremely low or nonexistent, and methanol will merely form an equilibrium mixture with its dehydration products dimethylether (DME) and water. At temperatures higher than about 900° F., the reaction mixture will tend to produce only methane and cracked products.

The reaction mixture may be mixed to provide a positive methanol concentration throughout the reaction zone, and preferably to maintain a substantially homogeneous reaction mixture composition, by the use of high levels of recycle of the reaction mixture in plug flow reactor systems or by backmixing of the reaction mixture in CSTR systems, for example.

Aromatic compounds are formed at high conversion conditions which favor olefin-olefin reaction due to depletion of available methanol, leading to cyclization of olefin-olefin reaction products. The resulting aromatic products are readily alkylated by methanol to form heavy aromatics. In general, a lower temperature requires the use of a lower space velocity, and vice versa. As is known in the art, temperature, pressure, space velocity, fluidizing or backmixing gas rates, and catalyst activity are interrelated.

In general, reaction conditions should be selected to result in a product containing no more than about 30 wt. % aromatic compounds, and preferably less than about 5 wt. % aromatics.

The use of relatively low temperatures, relatively high space velocity, and/or less active catalysts tend to minimize aromatics production and to lower conversion.

The process feed may, if desired, comprise pure methanol but in most cases will comprise a more dilute concentration (e.g. 5–10 wt. %, based on total gases) of methanol and may but need not contain olefins, typically $C_2$–$C_3$ olefins. In any event, methanol should be present in the feedstream in at least an equimolar ratio with respect to any olefins present, and preferably is present in at least a 2:1 molar ratio with respect to any olefins. Stated differently, methanol may comprise 50 to 100% of hydrocarbons present in the feedstream, and olefins may be present in an amount of up to 50% based on methanol present in the feedstream. The feedstream may be the product of another process, such as a Fischer-Tropsch synthesis gas conversion process or other syngas conversion process, and may contain one or more additional components or contaminants such as $H_2$, $N_2$, CO, $CO_2$, $H_2S$, low molecular weight (typically $C_1$–$C_4$) paraffinic hydrocarbons, or helium. $C_2$–$C_3$ olefins may be added to the feedstream, if desired.

It is preferred, however, that the feedstream does not contain ammonia, amines, or other basic materials which would tend to poison the acidic catalyst, or be contaminated with catalytically active metals such as transition metals (e.g. Ni, V) which would tend to promote conversion of methanol to methane.

The feedstream may contain other alcohols such as ethanol and propanol, in addition to methanol, if desired.

The catalyst may be any of a wide variety of solid acid catalysts having methanol conversion activity under the operating conditions of the inventive process. Suitable catalysts include, without limitation, shape selective catalysts known to have methanol conversion activity under other conditions as well, including ZSM-5 aluminosilicates, and AMS-1B and HAMS-1B borosilicate catalysts, for example.

However, the invention is suitable for utilizing other solid acid catalysts such as Y-zeolites or amorphous silica-alumina. Faujasite zeolites and silica-alumina comprising about 10 to about 90 wt. % silica, preferably about 70 wt. % silica, are especially preferred. In one form, a faujasite zeolite is dispersed in a matrix of alumina or silica-alumina. Alumina-expanded bentonite clay is suitable, as are a variety of other acid catalysts such as beta zeolites, L-zeolite (LTL), mordenite, mazzite (MAZ), FER, erionite, GME, MTW, and crystalline silicon-aluminum phosphate molecular sieves (SiAl-$PO_4$).

These and other useful catalysts are described in Meier, et al. (ed.), *Atlas of Zeolite Structure Types* (2nd Ed., Revised) published on behalf of the Structure Commission of the International Zeolite Association (Butterworths, 1987), the disclosure of which is incorporated herein by reference.

In general, it is preferred that the solid acid catalyst have medium to high Bronsted acidity, high activity, and preferably medium to wide pore diameter (i.e. greater than about 5, and preferably 6 to 8 angstroms) although catalysts having smaller pores may also be useful.

Among useful catalysts, crystalline or amorphous binary oxides, mordenite, zeolite L, beta zeolite, dealuminated (ultrastable) zeolites, and low alumina forms of amorphous silica-alumina are especially preferred. Y-zeolites, especially rare earth (REY) and other ion exchanged Y-zeolites and ultrastable Y-zeolites (USY) are particularly preferred. Dealuminated mordenite is also highly preferred.

One useful catalyst is AMS-1B crystalline borosilicate, and its hydrogen form HAMS-1B, which are described along with methods for the preparation in commonly assigned Klotz U.S. Pat. Nos. 4,268,420 (May 19, 1981) and 4,269,813 (May 26, 1981); Klotz, et al. U.S. Pat. No. 4,285,919 (Aug. 25, 1981); Miller, et al. U.S. Pat. No. 4,496,785 (Jan. 29, 1985); and European Patent Specification No. 68,796 (Sep. 17, 1988), all of which describe the preparation, characterization and utility of crystalline borosilicate catalysts and the respective disclosures of which are hereby incorporated by reference.

Useful crystalline borosilicate catalysts include those characterized by (a) the composition formula $$0.9 \pm 0.2 M_{2/n}O:B_2O_3:ySiO_2:zH_2O$$

wherein M is at least one cation having a valence n, y is between 4 and about 600, and z is between 0 and about 160, and (b) the following X-ray pattern wherein d-spacing is measured in terms of copper K alpha radiation and assigned strength is expressed in terms of VW=very weak, W=weak, M=medium, MS=medium strong, and VS=very strong:

| d-Spacing (Å) | Assigned Strength |
|---|---|
| 11.2 ± 0.2 | W–VS |
| 10.0 ± 0.2 | W–MS |
| 5.97 ± 0.07 | W–M |
| 3.82 ± 0.05 | VS |
| 3.70 ± 0.05 | MS |
| 3.62 ± 0.05 | M–MS |
| 2.97 ± 0.02 | W–M |
| 1.99 ± 0.02 | VW–M |

In the foregoing composition formula, M may be an alkali metal cation, an alkaline earth metal cation, an alkylammonium cation, a rare earth metal cation, a hydrogen cation, a catalytically active metal cation, or a mixture thereof. Cadmium is an especially preferred metal cation.

In the foregoing definition, the "assigned strength" of the interplanar d-spacing as determined by X-ray diffraction have been arbitrarily assigned as follows, based in relative peak heights:

| Relative Peak Height | Assigned Strengths |
|---|---|
| less than 10 | VM |
| 10–19 | W |
| 20–39 | M |
| 40–70 | MS |
| greater than 70 | VS |

The foregoing assigned strengths for interplanar spacings are based on non-calcined materials. Assigned strengths for materials calcined at 1000°–1100° F. are given in Klotz U.S. Pat. No. 4,268,420.

When contacted with the catalyst under methanol conversion conditions, methanol is subject to a dehydration reaction to form dimethyl ether (DME), and methanol in the reaction mixture will be maintained in equilibrium with dimethyl ether and water as a result of this reaction, resulting in a substantial dimethyl ether concentration in the reaction zone. It is unclear whether DME participates directly as an intermediate or otherwise in the simultaneously occurring reactions between methanol and hydrocarbon conversion products, but in any event methanol is consumed during the process.

Under reaction conditions, a portion of methanol is catalytically converted to $C_2$–$C_3$ olefins. Simultaneously, at least a portion of the remaining methanol in the reaction zone reacts with olefins present in the reaction mixture, whether supplied in the feedstream, by direct conversion of methanol to olefins, or the reaction of methanol with hydrocarbon conversion products, to produce higher molecular weight hydrocarbon products including $C_3$–$C_{12}$ linear and branched olefins and isoparaffinic gasoline components.

The reaction of methanol with hydrocarbons, particularly the reaction of methanol with $C_2$–$C_3$ olefins, is favored over reactions between olefins which result in undesirable coking of the catalyst. While over some catalyst such as ZSM-5, AMS-1B or HAMS-1B shape selective catalysts, $C_2$ and $C_3$ olefins will react with each other to form gasoline components, such low molecular weight olefins will, in the absence of methanol, react with each other to form coke over Y-zeolites, silica-alumina, and other solid acid catalysts. However, over the same Y-zeolite or silica-alumina catalysts, methanol can sequentially react with olefins to produce higher molecular weight olefins or paraffinic gasoline components, and much less coke than in prior processes using such catalysts.

Thus, it is important that a substantial concentration (e.g. at least about 5 wt. % based on total hydrocarbons) of methanol be available throughout the reaction zone for reaction with olefins, especially when using catalysts such as Y-zeolites and silica-alumina which have an undesirable tendency toward coke formation in the absence of methanol.

It is preferred to carry out the reaction at a selected temperature and for a sufficient period of time to result in olefins having 3 to 12 carbon atoms, especially $C_4+$ products, with the bulk of the product olefins having up to 8 or 9 carbon atoms with only traces up to 12. $C_4$ and $C_5$ olefins are especially valuable.

It is also preferred that the temperature and space velocity be such that the production of aromatic reaction products other than benzene, toluene and xylene, especially alkylated aromatic compounds such as durene, pentamethyl benzene, and hexamethyl benzene, are disfavored. Aromatics production is generally accompanied by the production of propane, which is also undesirable. Preferably, the product will contain a maximum of about 30% by weight, and preferably less than about 5 wt. % aromatic compounds.

The ability of the process to achieve the foregoing results under the disclosed reaction conditions is a direct result of maintaining a positive methanol concentration, and preferably a substantially homogeneous (within the limits of experimental error) gaseous reaction mixture composition throughout the reaction zone. The principal purpose of these conditions is to minimize and preferably substantially eliminate high concentrations of olefins and other reactive products relative to methanol within the reaction zone such that the reaction between methanol and olefins is favored over the olefin-to-olefin reaction which results in coking.

Homogeneity of reaction zone gaseous compositions may be provided by efficient mixing means which are well known to those skilled in the art. Whether accomplished by backmixing, recycle, or other means, the achievement of the benefits of the invention will increase directly with the uniformity of mixing provided.

For example, in a standard plug flow reactor with product recycle, the system has ideal plug flow character when there is zero recycle. When at infinite recycle, the system is ideally backmixed. In accordance with the invention, substantially complete (i.e. about 95 to about 98%) backmixing occurs with a recycle to feed ratio of greater than 10. The system is partially backmixed at recycle to feed ratios from 1 to 10, and some benefits of the invention will be achieved at recycle ratios of about 3:1 and more which will maintain positive methanol concentrations throughout the reactor.

From the foregoing description, it will be apparent to those skilled in the art that the inventive process provides means for extending the useful life of methanol conversion catalysts by preventing undesirable coke formation, and provides a variety of useful methanol conversion catalysts which heretofore were limited in their usefulness for this purpose or which were not considered useful for methanol conversion.

While the inventors do not wish to be limited to the following theory, it is postulated that the improvements due to the maintenance of a positive methanol concentration and, preferably, a homogeneous reaction mixture result from the mechanism of molecular growth of methanol over acidic catalysts, especially those with medium to wide pore diameters. With relatively wide pore catalysts, molecular growth is believed to occur primarily by methanol alkylation, as follows, for example:

rather than by olefin polymerization:

Olefins react to form coke over large pore zeolites and silica-alumina in the absence of methanol.

In a vertical plug flow reactor, the methanol concentration is high and the olefin concentration is low at the top of the reactor, where methanol is introduced. Molecular growth is disfavored in this region. In the bottom of the reactor the methanol concentration is low and the olefin concentration is high. This also does not favor chain growth. Additionally, the catalyst deactivates rapidly in the bottom of the reactor due to coking. With a backmixed reactor, however, olefins are recirculated to the top of the catalyst bed and methanol is circulated to the bottom. Everywhere in the reactor, olefins can react with methanol to form products rather than coke. As a result catalyst lives can be improved, as well as activity and selectivity. Methanol is more efficiently converted to gasoline or low molecular weight olefins in a backmixed reactor.

EXAMPLES

The invention will be illustrated by reference to the following detailed examples, which are not to be understood to limit the scope of the invention. Throughout, data are expressed in wt. %, unless otherwise indicated. Reaction temperatures in the tables are in some cases followed by an indication of sampling times.

EXAMPLE 1

This example illustrates that using faujasite catalysts in a backmixed fluidized bed reactor greatly enhances the catalysts' activity and selectivity for gasoline fraction components, as opposed to a plug flow fixed bed reactor without backmixing or recycle.

In this example, the catalytic materials were commercially available catalysts containing a faujasite zeolite in a matrix of either silica-alumina or alumina. The first (Catalyst A) was approximately 6% rare earth exchanged Y-sieve in a silica/alumina matrix available from Englehard Manufacturing under the trade name HFZ-33. The second (Catalyst B) contained 50% Y-82 sieve in an alumina matrix manufactured by the Linde division of Union Carbide.

The fixed bed reactions were done in a tubular plug flow reactor, 485 mm long, with an inside diameter of about 12 mm. Methanol was injected via a syringe pump at 10.0 cc/hr into $N_2$ carrier gas. The catalyst charge was adjusted to give the desired weight hourly space velocity (WHSV).

Fluidized bed reactions were carried out in a backmixed CSTR catalytic cracking mini-pilot plant. Fluidization was maintained by passing 400 cc/min of $N_2$ into the bottom of the reactor. Methanol feed was injected via syringe pump into 60 g of catalyst. The methanol flow rate was adjusted to attain the proper WHSV. In both systems the gas phase products were analyzed by gas chromatography.

Comparisons of the fixed and fluidized bed reactions for each catalyst are summarized on Tables 1 and 2, below.

Case 1 (Plug Flow Fixed Bed)

The fixed bed reactor was loaded with 7.91 g of Catalyst A (6% REY in silica-alumina) and the temperature was brought up to 370° C. in flowing $N_2$ at 5 cc/min. Methanol was pumped in at 7.91 g/hr (WHSV=1.0) and a gas syringe sample was taken after seven minutes on stream and analyzed by gas chromatography. The catalyst converted only 28.7% of the dimethyl ether (DME) to hydrocarbons. Table 1, case 1 summarizes the analytical data for this run. The numbers in parentheses convert the weight percentages of each component on a 100% DME conversion basis for easier comparison with fluidized bed (case 2). The light gas ($C_1$–$C_3$) make was quite high, on this basis (43.2%), with relatively low yields of the $C_5+$ fraction (43.9%).

Case 2 (Backmixed CSTR Fluidized Bed)

The fluidized bed reactor was loaded with 60 g of the same catalyst as in case 1. $N_2$ flow at 400 cc/min was established to cause bed fluidization and temperature equilibrium was established at 370° C. Methanol was pumped in at 60 g/hr (WHSV=1.0) for a 20-minute period and the composite gas sample was collected and analyzed by gas chromatography. The catalyst converted 100% of the DME to hydrocarbon products. The $C_1$–$C_3$ hydrocarbons were 8.14% and 78.8% of the products formed were in the $C_5+$ fraction (aliphatic and aromatic). Essentially no deactivation via coke formation was observed over the course of the run.

Case 3 (Plug Flow Fixed Bed)

With a new charge of catalyst A and under conditions identical to case 1 except for a reaction temperature of 400° C., DME conversion was 27.5%. The $C_1$–$C_3$ gas yield increased, primarily due to a higher $CH_4$ yield, to 51.9% (based on a 100% DME conversion basis).

Case 4 (CSTR Fluidized Bed)

The catalyst in case 2 was regenerated at 675° C. in air. At a WHSV of 7 and 400° C., DME conversion was still complete (100%) and the $C_1$–$C_3$ gas yields are very low (7.96%) along with a very high conversion to $C_5+$ products (75.4%).

TABLE 1

| Catalyst | A | A | A | A |
|---|---|---|---|---|
| Reactor | Plug Flow Fixed Bed | CSTR Fluidized Bed | Plug Flow Fixed Bed | CSTR Fluidized Bed |
| Case | 1 | 2 | 3 | 4 |
| WHSV | 1 | 1 | 1 | 7 |
| Reaction Temp. | 370° C. 7 min. | 370° C. composite | 400° C. 15 min. | 400° C. 10 min. |
| C1 | 0.5 (1.7) | 0.43 | 2.7 (9.8) | 0.44 |
| C2 | 4.9 (17.1) | 0.48 | 4.8 (17.4) | 0.44 |
| C2= | | 0.58 | | 0.55 |
| C3 | 7.0 (24.4) | 1.78 | 6.8 (24.7) | 1.78 |
| C3= | | 4.87 | | 4.75 |
| i-C4 | 3.6 (12.5) | 6.53 | 1.8 (6.5) | 6.41 |
| n-C4 | 0.1 (0.3) | 2.17 | — | 2.18 |
| C4= | | 4.52 | | 8.10 |
| C5+ aliphatics | 12.6 (43.9) | 75.76 | 11.4 (41.4) | 72.38 |
| Aromatics | | 3.02 | | 2.98 |
| % DME converted | 28.7 (100) | 100.0 | 27.5 (100) | 100.0 |

Cases 5–7 (Plug Flow Fixed Beds)

The plug flow fixed bed reactor of Cases 1 and 3 was charged with 6.25 g of Catalyst B (Union Carbide 50% Y82/50% alumina) and the bed temperature brought up to 412° C. with a 5 cc/min $N_2$ purge. After reaching reaction temperature, methanol was injected at 7.9 g/hr (WHSV=1.26). Gas samples were analyzed at 5, 30, and 60 minutes after initial feed injection. DME conversion was very high (100%, 100%, and 91.2% respectively) in all three cases. Light gas make was significantly higher than in cases 1 or 3 with the $C_1$–$C_3$ fractions being 57.9% for the 5-minute sample, 53.8% for the 30-minute sample, and 65.8% (100% DME conversion basis) for the 60-minute sample. The $C_5+$ fraction was only 12.5%, 20.4%, and 23.8% respectively for the three gas samples.

Case 8 (CSTR Fluidized Bed)

The backmixed fluidized bed reactor system of Cases 2 and 4 was charged with 60 g of the same catalyst as in cases 5–7. A fluidization $N_2$ flow of 400 cc/min was established and the bed temperature brought up to 400° C. Methanol was then injected into the system at 420 g/hr (WHSV=7.0) and a gas sample was analyzed five minutes into the run. The catalyst converted 99.3% of the DME to product with 29.77% $C_1$–$C_3$ and the $C_5+$ fraction was 27.4%. In addition, 37.1% of the products were the single component isobutane.

TABLE 2

| Catalyst | B | B | B | B |
|---|---|---|---|---|
| Reactor | Plug Flow Fixed Bed | CSTR Fluidized Bed | Plug Flow Fixed Bed | CSTR Fluidized Bed |
| Case | 5 | 6 | 7 | 8 |
| WHSV | 1.26 | 1.26 | 1.26 | 7 |
| Reaction Temp. | 412° C. | 412° C. | 412° C. | 412° C. |
|  | 5 min. | 30 min. | 60 min. | 5 min. |
| C1 | 28.9 | 23.2 | 33.6 (36.8) | 0.35 |
| C2 | 14.6 | 17.4 | 12.6 (13.8) | 0.40 |
| C2= |  |  |  | 16.30 |
| C3 | 14.4 | 13.2 | 13.9 (15.2) |  |
| C3= |  |  |  | 3.63 |
| i-C4 | 25.7 | 22.5 | 8.4 (9.2) | 37.10 |
| n-C4 | 3.9 | 3.3 | 0.8 (0.9) | 4.33 |
| C4= |  |  |  | 1.29 |
| C5+ aliphatics | 12.5 | 20.4 | 21.7 (23.8) | 27.18 |
| Aromatics |  |  |  | 0.26 |
| % DME converted | 100.0 | 100.0 | 91.2 (100) | 99.3 |

Case 9 (CSTR Fluidized Bed)

The backmixed fluidized bed reactor system, of Cases 2, 4 and 8 was loaded with 60 g of support (70/30 amorphous silica/alumina), designated Catalyst C. With a $N_2$ flow rate of 400 cc/min and a reactor temperature of 370° C., methanol was injected at 240 g/hr. (WHSV=4.0). Results are shown in Table 3. The catalyst converted 93% of the DME to hydrocarbons with 46.38% $C_1-C_3$ and 27.8% $C_5+$. This case demonstrates that the sieve component of the catalyst is not necessary and that an acidic amorphous material will convert methanol to hydrocarbons.

TABLE 3

| Catalyst | C |
|---|---|
| Reactor | CSTR Fluidized Bed |
| Case | 9 |
| WHSV | 4 |
| Reaction Temp. | 370° C. |
|  | 5 min. |
| C1 | 0.25 (0.26) |
| C2 | 0.11 (0.12) |
| C2= | 17.38 (18.7) |
| C3 | 9.09 (9.8) |
| C3= | 16.31 (17.5) |
| i-C4 | 19.32 (20.8) |
| n-C4 | 1.11 (1.2) |
| C4= | 8.76 (9.4) |
| C5+ aliphatics | 25.60 (27.5) |
| Aromatics | 0.26 (0.28) |
| % DME converted | 93.0 (100) |

SUMMARY

It can be seen by the data in Tables 1 and 2 that a) faujasite type catalyst can be used to give high yield of olefins or gasoline blending components from methanol and b) their activities and selectivities can be dramatically improved to produce gasoline boiling range hydrocarbons in a backmixed fluidized bed reactor. With proper selections of catalyst and reaction conditions (temperature as WHSV) gasoline yields ($C_4+$) of up to 90% have been obtained.

In addition, Case 9 (Table 3) shows that in the backmixed fluidized bed reactor, high yields of hydrocarbons can also be formed from methanol with an amorphous acid catalyst, e.g. silica-alumina, alumina-expanded bentonite clay, etc.

EXAMPLES 2 and 3

Reactor I was a Berty CSTR fixed bed reactor. The catalyst was placed in center of the reaction chamber in a stationary basket. The gases were rapidly circulated continuously through the stationary catalyst bed. The concentration of reactants and products was uniform throughout the reactor.

Reactor II was a conventional, high pressure, once-through stationary bed plug flow reactor.

Catalyst D was a composition of 5% CdO supported on a 50% Ultrastable Y-zeolite (USY) dispersed in alumina. Catalyst E also contained 5% CdO supported on 30% Rare Earth exchanged Y-zeolite (REY) dispersed in alumina. Details of the catalyst preparation are given in Miller, et al. U.S. Pat. No. 4,496,785.

EXAMPLE 2

Catalyst D was evaluated in the backmixed Berty reactor at 400° C., 500 psig and 1.0 LHSV (about 0.5 WHSV) of methanol. The conversion was 96.7%. The $C_1-C_3$ gas make was 23.8% and the yield $C_4+$ hydrocarbons, most of which were isoparaffins, was 76.2%. With the same catalyst in a plug flow fixed bed reactor at 1.0 LHSV (about 0.5 WHSV) the conversion was lower at 42.0%. The lower conversion was despite the higher reaction pressure of 1000psig. Furthermore, because of the high methane yield (60.2% at 385° C.) it was not possible to increase the conversion by raising the reaction temperature. For the plug flow reactor the $C_1-C_3$ gas make was 75.9% and the $C_4+$ yield was 24.1%. This example demonstrates the higher conversion and better selectivity obtained in the fixed-bed back mixed reactor versus the plug flow reactor. The results are listed in Table 4.

TABLE 4

| CATALYST: 5% CdO on 50% USY/50% $Al_2O_3$ | | | |
|---|---|---|---|
| Reaction Conditions: | | | |
| Reactor | I | II | II |
| Temp., °C. | 400 | 385 | 375 |
| Pressure ($H_2$), psig | 500 | 1000 | 1000 |
| LHSV (MeOH) | 1.0 | 1.0 | 0.5 |
| Hydrocarbon Products, Wt. % | | | |
| $CH_4$ | 10.8 | 60.2 | 66.4 |
| $C_2H_4$ | 4.4 | 5.0 | 1.9 |
| $C_2H_6$ | 1.1 | 3.1 | 1.9 |
| $C_3H_6$ | 2.2 | 2.1 | 0.4 |
| $C_3H_8$ | 5.3 | 5.5 | 4.5 |
| $iC_4H_{10}$ | 23.3 | 8.6 | 6.8 |
| $nC_4H_{10}$ | 1.6 | 2.6 | 2.3 |
| $iC_5H_{12}$ | 17.8 | 6.9 | 6.1 |
| $nC_5H_{12}$ | 1.6 | 0.9 | 0.8 |
| $C_6+$ | 32.6 | 5.1 | 8.9 |
| MeOH (dimethylether) Conversion | 96.7 | 42.0 | 73.2 |

EXAMPLE 3

Catalyst E was also evaluated in two separate experiments in the backmixed, fixed bed Berty reactor. In the first experiment the catalyst was run continuously for fifteen days at 500psig and 1.0 LHSV (about 0.5 WHSV). Over the fifteen days the temperature was increased from 385° C. to 415° C. to maintain the conversion above 85%. The same catalyst was also evaluated in a plug flow reactor at 360° C. and 500 psig. Even at 0.2 LHSV (about 0.1 WHSV) the conversion, 75.6%, was less than that obtained at 1.0 LHSV (about 0.5 WHSV) in the back-mixed reactor. Again in Reactor I the $C_1$-$C_3$ yields were lower (13.5% versus 33.5%) and $C_4+$ yields and higher (86.5% versus 66.5%) than for Reactor II. In addition, in Reactor I it was possible to continue the methanol reaction for over fifteen days while in Reactor II the catalyst deactivated in two days, despite the lower feed rates in Reactor II. The results are detailed in Table 5.

The results from these experiments indicate that the beneficial results of of the invention are the result of methanol reactions conducted in a backmixed (CSTR) reactor, either fixed bed or fluidized bed, and not the result of use of the fluid bed alone.

TABLE 5

CATALYST: 5% CdO on 30% REY/70% $Al_2O_3$

| Reaction Conditions: | | | | | | |
|---|---|---|---|---|---|---|
| Reactor | I | I | I | II | II | II |
| Temp., °C. | 385 | 400 | 415 | 370 | 370 | 360 |
| Pressure ($H_2$), psig | 500 | 500 | 500 | 500 | 500 | 500 |
| LHSV (MeOH) | 1.0 | 1.0 | 1.0 | 1.0 | 1.0 | 0.2 |
| Days | 1 | 5 | 15 | 1 | 4 | 8 hrs |
| Hydrocarbon Products, Wt. % | | | | | | |
| $CH_4$ | 5.2 | 4.3 | 14.5 | 6.1 | 6.6 | 16.6 |
| $C_2H_4$, $C_2H_6$ | 1.6 | 3.9 | 7.9 | 2.8 | 3.5 | 8.8 |
| $C_3H_6$ | 1.6 | 3.7 | 5.3 | 2.4 | 1.7 | 2.4 |
| $C_3H_8$ | 5.1 | 4.3 | 5.0 | 3.5 | 3.9 | 5.7 |
| $iC_4H_{10}$ | 31.2 | 33.2 | 19.8 | 37.4 | 29.3 | 33.7 |
| $nC_4H_{10}$ | 2.9 | 3.2 | 2.7 | 2.4 | 1.3 | 2.6 |
| $iC_5H_{12}$ | 12.7 | 17.9 | 16.8 | 19.6 | 19.0 | 17.9 |
| $nC_5H_{12}$ | 0.7 | 0.7 | 0.7 | 1.0 | 1.1 | 0.7 |
| $C_6+$ | 39.0 | 28.8 | 27.3 | 24.8 | 33.6 | 11.6 |
| MeOH (dimethylether) Conversion | 97.9 | 86.2 | 86.2 | 95.1 | 93.4 | 75.6 |

The foregoing detailed description is given for clearness of understanding only, and no unnecessary limitations should be understood therefrom, as modifications within the scope of the invention will be apparent to those skilled in the art.

We claim:

1. A process for converting a methanol feedstream comprising at least one mole of methanol per mole of any olefins present in said feedstream to a hydrocarbon product selected from $C_3$-$C_{12}$ olefins and paraffinic gasoline components, said method comprising the step of:
   contacting, in a backmixed reaction zone having a recycle to feed ratio of greater than about 3:1 and under methanol conversion conditions, a solid acid methanol conversion catalyst and a gaseous reaction mixture comprising said feedstream and conversion products thereof to form said hydrocarbon product selected from $C_3$-$C_{12}$ olefins and paraffinic gasoline components.

2. The process of claim 1 wherein a substantially homogeneous reaction mixture composition is maintained throughout said reaction zone.

3. The process of claim 2 wherein said reaction mixture composition is maintained substantially homongeneous by employing a recycle to feed ratio greater than about 10:1.

4. The process of claim 1 wherein said reaction mixture comprises methanol in equilibrium with dehydraton products thereof, olefins, and said hydrocarbon product resulting from reaction of said methanol with said olefins.

5. The process of claim 4 wherein a portion of said methanol is catalytically converted to $C_2$-$C_3$ olefins, and another portion if said methanol simultaneously reacts with olefins present in said reaction mixture to produce said hydrocarbon product selected from $C_3$-$C_{12}$ olefins and paraffinic gasoline components.

6. The process of claim 1 wherein said conversion conditions include a temperature in the range of about 600° to about 900° F., a pressure in the range of atmospheric pressure to about 500 psig, and a weight hourly space velocity of about 0.1 to about 20 $hr^{-1}$.

7. The process of claim 6 wherein said conversion conditions include a temperature in the range of about 675° to about 775° F., a pressure in the range of atmospheric pressure to about 100 psig, and a weight hourly space velocity in the range of about 1 to about 5 $hr^{-1}$., and wherein the molar ratio of said methanol to any $C_2$-$C_3$ olefins present in said feedstream is at least about 2:1.

8. The process of claim 1 wherein said catalyst has an average pore diameter of at least about 5 angstroms.

9. The process of claim 8 wherein said catalyst has an average pore diameter of about 6 to about 8 angstroms.

10. The process of claim 8 wherein said catalyst is selected from silica-alumina and Y-zeolite catalysts.

11. The process of claim 8 wherein said catalyst is selected from mordenite, binary oxides, beta zeolites, zeolite L, MAZ, alumina-expanded bentonite clay, USY, REY, ZSM-5, FER, GME, MTW, erionite and crystalline silicon-aluminum phosphate molecular sieves.

12. The process of claim 8 wherein said catalyst comprises a crystalline borosilicate characterized by
   (a) the composition formula

$$0.9 \pm 0.2 M_{2/n}O : B_2O_3 : ySiO_2 : zH_2O$$

wherein M is at least one cation having a valence n, y is between 4 and about 600, and z is between 0 and about 160, and
   (b) the following X-ray pattern wherein d-spacing is measured in terms of copper K alpha radiation and assigned strength is expressed in terms of VW=very weak, W=weak, M=medium, MS=medium strong, and VS=very strong:

| d-Spacing (Å) | Assigned Strength |
|---|---|
| 11.2 ± 0.2 | W-VS |
| 10.0 ± 0.2 | W-MS |
| 5.97 ± 0.07 | W-M |
| 3.82 ± 0.05 | VS |
| 3.70 ± 0.05 | MS |
| 3.62 ± 0.05 | M-MS |
| 2.97 ± 0.02 | W-M |
| 1.99 ± 0.02 | VW-M |

13. The process of claim 1 wherein said feedstream comprises methanol and $C_2$-$C_3$ olefins.

14. The process of claim 13 wherein said feedstream is the product of a synthesis gas conversion process.

15. The process of claim 14 wherein said feedstream contains one or more additional components selected from CO, $CO_2$, $H_2$, $H_2S$, $C_1$-$C_4$ paraffinic hydrocarbons, nitrogen, and helium.

16. The process of claim 1 wherein said contacting step is carried out for a sufficiently short time period and under conditions selected such that said product comprises a maximum of about 30% by weight aromatic compounds.

17. The process of claim 1 wherein said reaction zone is defined by a reactor selected from the group consisting of backmixed fixed bed and fluidized bed reactors.

18. A process for converting a methanol feedstream comprising at least one mole of methanol per mole of any olefins present in said feedstream to a hydrocarbon product selected from $C_3$–$C_{12}$ olefins and paraffinic components, said method comprising the step of:

contacting, in a backmixed reaction zone having a recycle to feed ratio of greater than about 3:1 and under methanol conversion conditions including a temperature in the range of about 600 to about 900° F., a pressure in the range of atmospheric pressure to about 500 psig, and a weight hourly space velocity of about 0.1 to about 20 $hr^{-1}$, a solid acid methanol conversion catalyst having an average pore diameter of at least about 5 angstroms and a gaseous reaction mixture comprising methanol from said feedstream in equilibrium with dehydration products thereof, $C_2$–$C_3$ olefins, and said hydrocarbon product resulting from reaction of said methanol with said olefins to form said hydrocarbon product selected from $C_3$–$C_{12}$ olefins and paraffinic gasoline components.

19. The process of claim 18 wherein a substantially homogeneous reaction mixture composition is maintained throughout said reaction zone by employing a recycle to feed ratio greater than about 10:1.

20. The process of claim 18 wherein a portion of said methanol is catalytically converted to $C_2$–$C_3$ olefins, and another portion of said methanol simultaneously reacts with olefins present in said reaction mixture to produce said hydrocarbon product selected from $C_3$–$C_{12}$ olefins and paraffinic gasoline components.

21. The process of claim 18 wherein said conversion conditions include a temperature in the range of about 675° to about 775° F., a pressure in the range of atmospheric pressure to about 100 psig, and a weight hourly space velocity in the range of about 1 to about 5 $hr^{-1}$., and wherein the molar ratio of said methanol in said feedstream to any $C_2$–$C_3$ olefins present in said feedstream is at least about 2:1.

22. The process of claim 18 wherein said catalyst has an average pore diameter of about 6 to about 8 angstroms.

23. The process of claim 18 wherein said catalyst is selected from silica-alumina and Y-zeolite catalyst.

24. The process of claim 18 wherein said contacting step is carried out for a sufficiently short time period and under conditions selected such that said product comprises a maximum of about 30% by weight aromatic compounds.

25. The process of claim 18 wherein said reaction zone is defined by a reactor selected from the group consisting of backmixed fixed bed and fluidized bed reactors.

26. A process for converting a methanol feedstream comprising at least one mole of methanol per mole of any olefins present in said feedstream to a hydrocarbon product selected from $C_3$–$C_{12}$ olefins and paraffinic gasoline components, said method comprising the step of:

contacting, in a reaction zone defined by a reactor selected from the group consisting of backmixed fixed bed and fluidized bed reactors having a recycle to feed ratio of greater than about 3:1 and under methanol conversion conditions including a temperature in the range of about 600° to about 900° F., a pressure in the range of atmospheric pressure to about 500 psig, and a weight hourly space velocity of about 0.1 to about 20 $hr^{-1}$, a silica-alumina or Y-zeolite methanol conversion catalyst having an average pore diameter of at least about 5 angstroms and a gaseous reaction mixture comprising methanol from said feedstream in equilibrium with dehydration products thereof, $C_2$–$C_3$ olefins, and said hydrocarbon product resulting from reaction of said methanol with said olefins whereby a portion of said methanol is catalytically converted to $C_2$–$C_3$ olefins and another portion of said methanol simultaneously reacts with olefins present in aid reaction mixture to produce said hydrocarbon product selected from $C_3$–$C_{12}$ olefins and paraffinic gasoline components, said contacting step being carried out for a sufficiently short time period and under conditions selected such that said product comprises a maximum of about 30% by weight aromatic compounds.

27. The process of claim 26 wherein a substantially homogeneous reaction mixture composition is maintained throughout said reaction zone by backmixing or recycling of said reaction mixture at a recycle to feed ratio of greater than about 10:1.

28. The process of claim 26 wherein said conversion conditions include a temperature in the range of about 675° to about 775° F., a pressure in the range of atmospheric pressure to about 100 psig, and a weight hourly space velocity in the range of about 1 to about 5 $hr^{-1}$., and wherein the molar ratio of said methanol in said feedstream to any $C_2$–$C_3$ olefins present in said feedstream is at least about 2:1.

29. The process of claim 26 wherein said catalyst has an average pore diameter of about 6 to about 8 angstroms.

* * * * *